United States Patent [19]

Chan

[11] Patent Number: 6,004,486
[45] Date of Patent: Dec. 21, 1999

[54] PHOTOCHROMIC SPIROXAZINES WITH ASYMMETRIC MONOCYCLIC SUBSTITUENT, COMPOSITIONS AND ARTICLES CONTAINING THEM

[75] Inventor: You-Ping Chan, Lyons, France

[73] Assignee: Corning Incorporated, Corning, N.Y.

[21] Appl. No.: 09/011,162

[22] PCT Filed: Sep. 6, 1996

[86] PCT No.: PCT/US96/14377

§ 371 Date: Feb. 2, 1998

§ 102(e) Date: Feb. 2, 1998

[87] PCT Pub. No.: WO97/10241

PCT Pub. Date: Mar. 20, 1997

[30] Foreign Application Priority Data

Sep. 11, 1995 [FR] France ................................. 95/10618

[51] Int. Cl.⁶ ..................... C07D 413/02; C07D 413/04; C07D 413/14
[52] U.S. Cl. .......................... 252/586; 351/163; 359/241; 359/242; 359/674; 359/885; 430/340
[58] Field of Search ............... 544/71; 252/586; 351/163

[56] References Cited

U.S. PATENT DOCUMENTS 5,139,707  8/1992  Guglielmetti et al. ............... 252/586

OTHER PUBLICATIONS

Tateoka et al., Chemical Abstracts, vol. 111, abstract 87504z, 1989.
Murayama et al., Chemical Abstracts, vol. 114, abstract 133085a, 1991.

*Primary Examiner*—Richard L. Raymond
*Attorney, Agent, or Firm*—Angela N. Nwaneri; Peter Rogalskyj

[57] ABSTRACT

The invention concerns photochromic compounds with the following Formula:

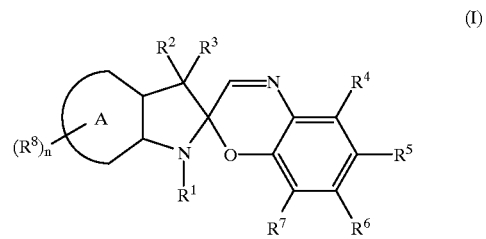

(I)

in which:

$R^1$ is a asymmetric aliphatic monocyclic group with the Formula,

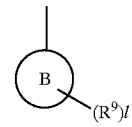

where $l=1-12$, and $R^9$ is H or an alkyl, alkoxy, dialkylamino, alkyl ester or CN group with the condition that at least one of the $R^9$ groups is not H, $R^2$–$R^7$ can have a variety of meanings, A represents a (hetero)aromatic ring which can be substituted and n is a whole number.

Application to the production of photochromic articles made of organic polymer, notably lenses.

28 Claims, No Drawings

PHOTOCHROMIC SPIROXAZINES WITH ASYMMETRIC MONOCYCLIC SUBSTITUENT, COMPOSITIONS AND ARTICLES CONTAINING THEM

This application is a 371 of PCT/US96114377, filed Sep. 6, 1996.

The present invention concerns novel compounds of the spiroxazine type presenting, in particular, photochromic properties. It also concerns the photochromic compositions and ophthalmic articles (e.g., lenses) which contain spiroxazines.

The photochromic compounds are capable of changing color due to the influence of a poly- or monochromatic light (e.g., UV) and they are capable of covering their initial content, when the irradiation with light stops, or due to the influence of a poly- or monochromatic light which is different from the first light, or due to the influence of the temperature and/or of a poly- or monochromatic light which is different from the first one.

These photochromic compounds are applied in various fields, for example, for the manufacture of ophthalmic lenses, contact lenses, some sunshades, filters, optics for cameras or photography apparatuses or other optical devices or observation devices, glass partitions, decorative objects, elements of displays or for the storage of information by optical inscription (encoding).

In the field of ophthalmic optics, and in particular in the field of eyeglasses, a photochromic lens, comprising one or more photochromic compounds, must present:

- a high transmission in darkness or in the absence of sunlight,
- a low transmission (high colorability) when exposed to irradiation by sunlight,
- an appropriate kinetics of coloration and decoloration,
- a tint which is acceptable to the consumer (gray or chestnut brown, preferably), with, preferably, maintenance of the selected tint during the course of the coloration and the decoloration of the lens,
- a maintenance of the performances of the characteristics in a temperature range of 0–40° C.,
- a high durability, because the objectives intended are sophisticated and, therefore expensive, corrective lenses.

These lens characteristics are in fact determined by the active photochromic compounds which, in addition, must be perfectly compatible with the organic or mineral support which constitutes the lens.

Moreover, it should be noted that the obtention of a gray or chestnut brown tint may require the use of at least two photochromes of different colors, that is having distinct maximum absorption wavelengths in the visible range ($\lambda_{max}$). This association thus imposes still other requirements on photochromic compounds. In particular, the kinetics of coloration and decoloration of the two or more associated active photochromic compounds must be essentially identical. The same applies to their stability over time and, also, to their compatibility with a plastic or mineral support.

Among the numerous photochromic compounds described in the prior art, one can cite the indolinospironaphtoxazines described in U.S. Pat. Nos. 3,578,602, 3,562,172, 4,215,010; European Patent Nos. 0,171,909, 0,313,941, French Patent No. 2,647,789; European Patent No. 0,600, 669:

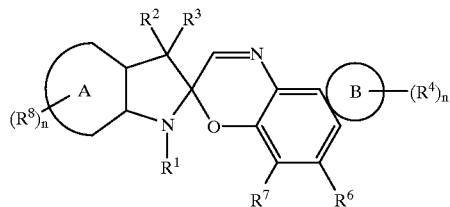

The group $R_1$ of these molecules represent linear or branched alkyls, alkylaryls or alicyclics. These compounds are considered to meet the specifications defined above.

In fact, while these compounds have indeed one or more of the wanted basic properties, such as high transmission in darkness, high colorability when exposed to sun radiation, absorption in the blue or violet [spectrum] (570–630 nm), rapid kinetics of coloration and decoloration, all the compounds described to this day do not have the complete combination of the desired properties that are required for the production of satisfactory articles, which can be manufactured industrially.

Whereas the prior art teaches how to modify the absorption band by the addition of substituents to the different positions of the rings and also how to modify the kinetics of decoloration, in contrast, it does not teach how to increase the colorability of these molecules without increasing the residual coloration in the inactivated state and, above all, on how to make them photochemically stable so as to allow their use on an industrial scale. Indeed, without a high stability, these expensive molecules, introduced into a sophisticated lens, cannot be used.

It is the merit of the applicant to have found unexpectedly that the presence of an asymmetric monocyclic substituent group on the nitrogen atom of the indoline or portion of certain indolinospiroxazines allows the solution of the problem of the residual coloration and of the colorability, which is essential for the indicated applications.

The originality of the invention resides in the surprising effect of the asymmetric monocyclic group which increases the colorability of the spiroxazines, without increasing their residual coloration, while ensuring a good photostability.

Thus, the present invention concerns a compound, in particular, a photochromic compound, having the following General Formula (I):

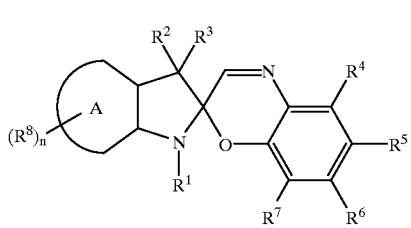

(I)

in which, $R^1$ is an asymmetric aliphatic monocyclic group which is directly connected to the nitrogen atom, having from 5 to 7 members, and possibly comprising at least one heteroatom, and having the Formula

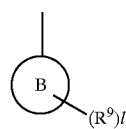

where l=1–12, $R^9$ represents H or an alkyl, alkoxy, dialkylamino, alkyl ester or CN group, provided that at least one of the $R^9$ is not H.

$R^2$, $R^3$ are identical or different and they represent an alkyl group, linear or branched, of 1–12 carbon atoms, an alkenyl, alkynyl, aryl, alkylaryl, cycloalkyl, $R^2$ and $R^3$ can, optionally, combine to form a carbocyclic or heterocyclic group having 5 to 10 atoms, $R^4$, $R^5$, $R^6$ and $R^7$ are identical or different and they represent:

hydrogen, an alkyl, cycloalkyl, alkenyl alkynyl, aryl (preferably phenyl, naphthyl mono-, di- or trisubstituted by electron donor or acceptor groups), heteroaryl, aryloxy or aralkyl, said group being optionally halogenated, a halogen, preferably F, Br, Cl, OR, SR, —OCOR, —COOR, with R=H alkyl and/or cycloalkyl and/or aryl a (poly)ether, a (poly)amide, a (polycarbonate, a (poly)carbamate, a (poly)urea or a (poly)ester, an amino radical which gives rise, once it is bound in (I), to a primary, secondary or tertiary amine, said amine being alkyl, aryl or aralkyl, mono- or disubstituted depending on its nature, or an aminocyclic radical containing, optionally, one or more heteroatoms, or an electron withdrawing group selected, preferably, from the group comprising $CF_3$, CN, $NO_2$, SCN, where at least two of the radicals $R^4$, $R^5$, $R^6$, $R^7$, preferably borne by two adjacent carbon atoms, can combine to form at least one aromatic ring having 5 or 6 members or aliphatic ring having 5 to 7 members, preferably 5 or 6 members, said ring(s) comprising, optionally, at least one heteroatom, so as to form at least one heterocyclic ring, the latter being optionally substituted by one or more radicals, which may be identical or different, and have the same definition as given above for $R^4$ to $R^7$, A represents a (hetero)aromatic ring (containing, for example, at least one nitrogen atom) and possibly substituted by one or more radicals $R^8$, which may be identical or different, and having the same definition as given above for $R^4$ to $R^7$, n is a whole number and when n≦2, two of the radicals $R^8$ can possibly combine to form at least one aromatic or heteroaromatic ring.

The term "asymmetric" in the expression "asymmetric aliphatic monocyclic group" signifies that the plane which is perpendicular to the ring B of group $R^1$ and including the segment of a straight line representing the bond between the ring B and the nitrogen atom is not a plane of symmetry for the group $R^1$, with the understanding that this reasoning is based on the formula developed in a plane of the group $R^1$.

Specific examples of groups $R^1$ are the following:

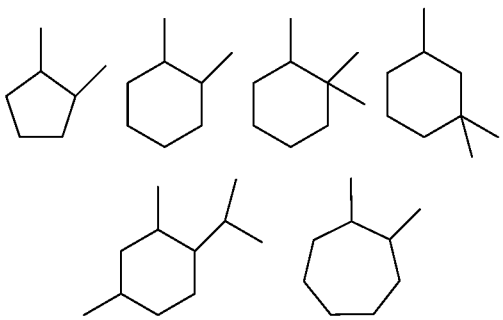

among many others.

Preferred compounds of the invention have the following Formula (I'):

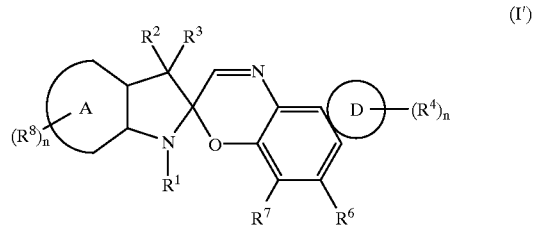

where A, and $R^1$ to $R^7$ are as defined above, and D is an aromatic or aliphatic ring having 5 to 7 members, optionally comprising a heteroatom, which may or may not be substituted by one or more radicals, which may be identical or different, and have the same definition as given for $R^4$ to $R^7$.

According to a particularly preferred embodiment of the invention, the ring A is a phenyl group and $R^4$ and $R^5$ combine to form an aromatic ring. This corresponds to the following

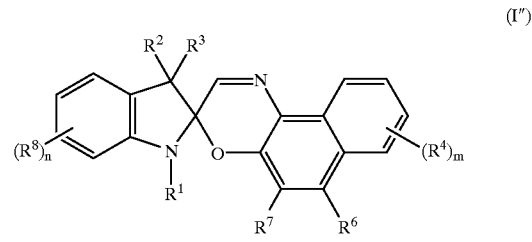

in which $R^1$ to $R^4$ and $R^6$ to $R^8$ are as defined above, and n and m assume the values 0 to 4.

Among the substituents which can be considered for the compounds with Formulas (I), (I') and (I") according to the invention, groups $R^4$ to $R^9$ must be considered which comprise and/or form at least one reactive function for polymerization and/or crosslinking, selected, preferably, from the following list: alkenyl—preferably vinyl—methacryloyl, acryloyl, acryloxyalkyl, methacryloxyalkyl or epoxy.

Thus, the photochromic compounds according to the invention can be designed as monomers, of different types or not, which can react between themselves or with other comonomers, to form homopolymers and/or copolymers, which bear a photochromic group and which have the mechanical properties of macromolecules. It follows that one of the objects of the present invention consists of these homopolymers or copolymers comprising (co)monomers and/or of crosslinkages, consisting at least in part of photochromic compounds (I), (I') and (I") according to the invention.

In the same order of ideas, the above-mentioned compounds (I), (I') and (I") can be considered to be crosslinking agents which have reactive functions capable of allowing the formation of bridges between polymer chains which may or may not be of photochromic type. The crosslinkages, which can thus be obtained, also constitute another object of the present invention.

In general in the preceding formulas, the following designations are used, according to the invention:

"alkyl," referring preferably to a linear or branched hydrocarbon group having from 1 to 12 carbon atoms;

"alkoxyl," referring to a group of O-alkyl type preferably having from 1 to 10 carbon atoms, "aryl," referring to an aromatic hydrocarbon group containing at least 6 carbon atoms, "heteroaryl," referring to an aromatic hydrocarbon group comprising of at least 5 atoms, of which at least one is a heteroatom, "aralkyl," a group comprising of at least one alkyl and at least one aryl, as defined above, "heteroatom," atoms different from C and H, belonging preferably to the following group: N, O, and S.

The photochromic compounds used which are particularly preferred in the context of the invention are thus, as can be concluded from the above, indolinospironaphthoxazines or indolinospirobenzoxines.

The most advantageous indolinospiroxazines include those having the Formula:

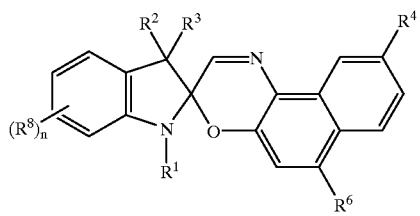

where $R^1$ =

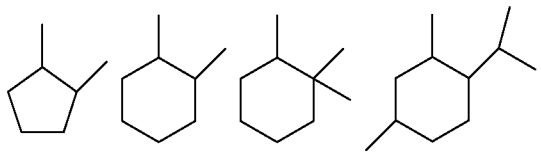

n=0, 1 or 2 and
$R^2$, $R^3$=$C_1$–$C_5$ alkyl,
$R^4$=H, OMe,
$R^6$=H, OMe or amino,
$R^8$=H, Me, OMe or $CF_3$.

It is the merit of the applicant to have disclosed these compounds, because they present particularly advantageous photochromic properties. More specifically, they have high colorability, particularly in the blue region of the spectrum. They are thus well suited to combination—observing compatibility and complementarity requirements—with photochromes which absorb in the yellow, orange, red and violet spectra, so as to obtain a broad coverage of the visible absorbance spectrum and thus coloration tints which are just chestnut brown or dark gray.

The sensitivity, as well as the height and the area of their $\lambda_{max}$ peaks in the visible range reach satisfactory values.

These compounds are also perfectly stable and compatible with support matrices made of organic polymers or of mineral material, both in a form included in the matrix and in the form of a coating.

In solution, or in a polymer matrix, the compounds according to the invention are colorless or slightly colored in the initial state and rapidly develop an intense coloration under UV light (365 nm) or a light source of the sun radiation type. Finally, they quickly restore their initial color when the irradiation stops.

The compounds of the invention can be obtained by the condensation of an indoline derivative substituted with an asymmetric aliphatic monoclyclic group $R^1$ and an aromatic nitroso alcohol derivative such as those described, for example, in U.S. Pat. Nos. 3,578,602, 4,634,767, 4,913,544 and European Patent No. A 600,669. This reaction can take place in solvents such as ethanol, toluene or dichloroethane.

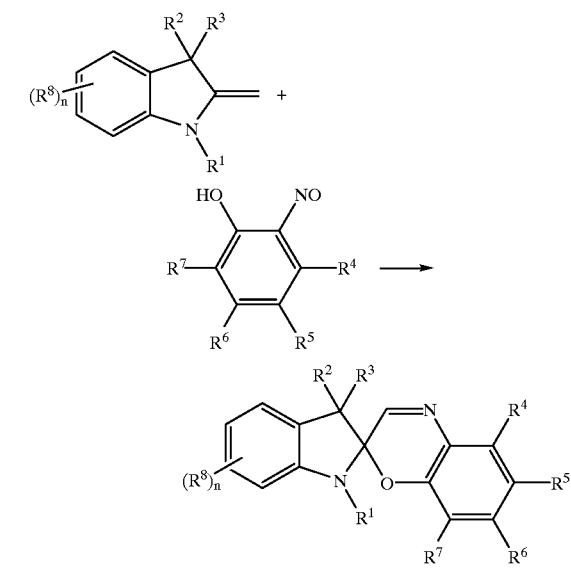

The indoline derivatives are obtained by methods which are adapted from the literature.

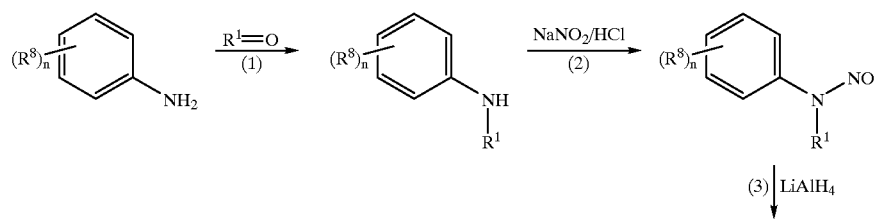

-continued

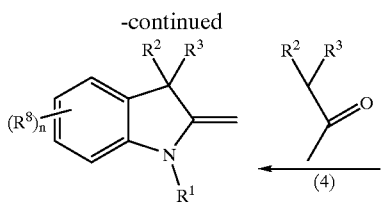

Step 1 is performed according to a procedure described in Katritzky et al., Tetrahedron, 1991, Vol. 47, p. 2683. The nitrosation of the amine (step 2) is conducted by a reaction with sodium nitrite-hydrochloric acid and the reduction of the nitroso derivative (step 3) is conducted by the reaction of $LiAlH_4$ in THF (Fridman et al., Russian Chemical Reviews, 1971, 40(1), 34). The last step of the synthesis (4) is conducted by reacting hydrazine with the appropriate ketone in an acidic medium, for example, hydrochloric acid/ethanol or acetic acid (for a general review of this reaction one can consult Robinson "Fischer indole synthesis," Wiley-Interscience, 1982).

In the case of applications of compounds according to the present invention, it should be noted that they can be used as a photochromic material which is dispersed in the superficial part or in the composition of a polymer or mineral matrix. They can also be used in solution.

A photochromic solution can be obtained by dissolving the compound in an organic solvent, such as toluene, dichloromethane, tetrahydrofuran or ethanol. The solutions obtained are in general colorless and transparent. When exposed to sunlight, they developed a strong coloration and their colorless state is restored when they are placed in a zone with less exposure to solar radiation or, in other words, when they are no longer exposed to UV radiation. In general, it is sufficient to use a very small concentration of product (on the order of 0.01–5%) to obtain an intense coloration.

The most intense applications are those in which the photochrome is dispersed uniformly within or on the surface of a polymer, copolymer or mixture of polymers. A great variety of methods of implementation can be considered. Those known to persons skilled in the art include, for example, diffusion in the (co)polymer, from a suspension or solution of the photochrome, in a silicone oil, in an aliphatic or aromatic hydrocarbon, in a glycol, or from another polymer matrix. The diffusion is routinely conducted at a temperature of 50–200° C. for a duration of 15 min to several hours, depending on the nature of the polymer matrix.

Another implementation technique consists in mixing the photochrome in a formulation of polymerizable substances, in depositing this mixture on a surface or in a mold and then conducting the polymerization.

These implementation techniques and others are described in the article by CRANO et al. "Spiroxazines and their use in photochromic lenses" published by Applied Photochromic Polymer Systems, Published by Blackie and Son Ltd—1992.

According to a variant of the invention, it is also possible to consider grafting the photochromes onto (co)polymers. Thus, another object of the invention consists of (co)polymers to which at least one of the photochromes described above has been grafted.

Examples of preferred polymer materials for the optical applications of the photochromic compounds according to the invention include the following products:

polyacrylate or polymethacrylate of alkyl, of cycloalkyl, of aryl or of arylalkyl (mono, di, tri or tetra), optionally halogenated or comprising of at least one ether and/or ester and/or carbonate and/or carbamate and/or thiocarbamate and/or urea and/or amide group(s), polystyrene, polycarbonate (e.g., bisphenol-A polycarbonate, allyl polycarbonate diethylene glycol, polyepoxy, polyurethane, polythiourethane, polysiloxane, polyacrylonitrile, polyamide, aliphatic or aromatic polyester, vinyl polymers, cellulose acetate, cellulose triacetate, cellulose acetate propionate or polyvinylbutyral, copolymers of two or several types of monomer or mixtures of polymers mentioned above, preferably polycarbonate-polyurethane, poly(meth)acrylatepolyurethane, polystyrene-poly(meth)acrylate or polystyrene-polyacrylonitrile, preferably a mixture of polyester or of polycarbonate or of poly(meth)acrylate.

The quantity of photochrome used depends on the desired degree of darkening. Usually a quantity of 0.001–20 wt % is used.

The photochromic compounds according to the invention can be used alone or in a mixture with other products to form a composition which can be in solid or liquid form, for example, in a solution or in a dispersion, as already indicated above. These compositions, which constitute another object of the invention, can thus comprise the compounds (I), (I') and (I") of the invention and other complementary photochromic compounds which allow the obtention of dark colorations, for example, gray or brown, which are desired by the public in applications such as ophthalmic or sun protection eyewear. These complementary photochromic compounds have an $\lambda_{max}$ and an absorbance spectrum in visible such that after association with the compounds of the invention, impart the desired tint to the mixture of the activated photochromes.

The photochrome(s), which can be associated with the compounds of the invention, is/are those known to a person skilled in the art and described in the literature, for example, chromenes (U.S. Pat. Nos. 3,567,605, 5,238,981; World Patent No. 9,422,850; European Patent No. 0,562,915), spiropyranes or naphthospyropanes [sic] (U.S. Pat. No. 5,238,981) and spiroxazines (J. C. CRANO et al., "Applied Photochromic Polymer Systems," Publisher Blackie & Son Ltd., 1992, Chapter 2).

These compositions according to the invention can also comprise:

nonphotochromic dyes which allow an adjustment of the tint, and/or one or more stabilizers, such as, for example, an antioxidant, and/or one or more anti-UV agents, and/or one or more antiradical compounds, and/or one or more deactivators of photochemically excited states.

These additives can allow an improvement of the durability of said compositions.

According to another of its aspects pertaining to the application of the photochromic compounds (I), (I') and (I"), the present invention also relates to ophthalmic articles, such as articles of ophthalmic or sun protection eyewear, comprising at least one compound according to the invention and/or at least one (co)polymer formed, at least in part, of recurrent units of type (I), (I') or (I") and/or at least one composition comprising the compounds (I), (I') or (I") according to the invention, as defined above, and/or at least one matrix, as defined above, made of an organic polymer material or of a mineral material or of a mineral-organic hybrid material incorporating at least a compound of the invention.

In practice, the articles which are most referred to by the present invention are photochromic ophthalmic or sunprotection lenses, window panes (windows for buildings, for locomotives, automobiles), the optical devices, the decorative articles, the articles for sun protection, the storage of data, etc.

The present invention will be understood better in light of the following examples of photochromic synthesis and validation of compounds (I), (I') and (I') which it concerns.

EXAMPLES

Synthesis and Properties of Photochromic Compounds (1)–(4) according to the Invention (Examples 1–4)

The formulas of compounds (1)–(4) are given below (see Table I).

Example 1

Synthesis of Compound (1)

Step 1

Synthesis of 2-methylcyclohexylphenylamine

In a 100-mL flask, the following mixture is heated at reflux for 30 h: 9.3 g aniline, 11.2 g 2-methylcyclohexanone and 12 g benzotriazole. Then, 200 mL of methanol and 5 g of NaBH$_4$ in portions are added to the mixture, which is then heated at reflux for 30 min. The solution is allowed to cool, and 100 mL of water are added to the mixture, which is extracted with 2×100 mL diisopropyl ether. The organic phase is recovered, dried over magnesium sulfate and reduced to dryness. In this manner, 7 g of the desired amine are produced.

Step 2

Synthesis of 1-(2-methylcyclohexyl)-1-phenylhydrazine

The amine from the preceding step (7 g) is suspended in 100 mL of hydrochloric acid (1N), and then the mixture is maintained at 0° C. with stirring. An aqueous solution of NaNO$_2$ (2 g in 20 mL of water) is then added to the mixture in small portions. The temperature is then allowed to rise to the ambient temperature, and the nitroso derivative is extracted with 2×100 mL diisopropyl ether. After evaporation of the solvent, 8 g of product are recovered. This product is then added slowly and in small portions into tetrahydrofuran (80 mL) containing 3 g LiAlH$_4$ and, then, the mixture is heated at reflux for 1 h. The mixture is subsequently cooled to 0° C., and then the excess of hydride is neutralized with an aqueous soda solution. Next, 30 g Na$_2$SO$_4$ are added, and the organic phase is recovered by filtration and reduced to dryness. In this manner 7 g of the desired hydrazine are produced.

Step 3

Synthesis of the 2-methylene derivative

In a 100-mL flask, 7 g hydrazine from the preceding step and 3 g 3-methyl-2-butanone in 30 mL ethanol containing 1 drop of acetic acid at 50° C. are reacted. Then 5 mL concentrated hydrochloric acid are added, and the mixture is heated at reflux temperature for 10 min. The medium is then neutralized with soda and the indole derivative is extracted with 100 mL diisopropyl ether. After evaporation of the solvent, 3 g of the desired product are obtained.

Step 4

Synthesis of spiroxazine (1)

The product of the preceding step (3 g) and 1.8 g 1-nitroso-2-naphthol are dissolved in 30 mL ethanol, and then the mixture is heated at 70° C. for 30 min. The solvent is then evaporated under a vacuum, and the product is then isolated by chromatography on a silica column with toluene as eluant. The product obtained (1 g) is crystallized in heptane. 450 mg of a slightly green product are isolated. Its structure is confirmed by NMR spectroscopy.

Example 2

Synthesis of compound (2)

Step 1

In a 100-mL flask, the following mixture is heated at 120° C. for 24 h: 12 g 3,4-dimethylaniline, 11 g 2-methylcyclohexanone and 12 g benzotriazole. The 2-methylcyclohexyl-2,4-dimethylphenylamine is isolated after reduction, as in step 1 of Example 1. 18 g of an oily product are isolated.

Steps 2, 3 and 4

These steps are conducted as before. The spiroxazine (2) is synthesized from 3.5 g of the indoline derivative and 2.2 g 1-nitroso-2-naphthol in ethanol at 60° C. for 2 h. 1.5 g of product are isolated after chromatography. Its structure is confirmed by NMR spectroscopy. The latter shows the existence of several isomers, because of the position of the two methyls on the phenyl of the indole (4,5-dimethyl and 5,6-dimethyl derivative) and because of the position of the nitrogen on the ring (cis and trans with respect to the 2-methyl group).

Example 3

Synthesis of Compound (3)

Step 1

In a 250-mL flask, equipped with a Dean-Stark separator, the following mixture is heated at reflux: 12 g 3,4-dimethylaniline, 20 g menthone, 14 g benzotriazole and 200 mL toluene. After recovery of the theoretical quantity of water (16 h), the mixture is reduced to dryness and then dissolved in 200 mL methanol and the product is reduced with NaBH$_4$, as above. 25 g of an oily product are isolated.

Steps 2, 3 and 4

These steps were conducted as before, the spiroxazine (3) is synthesized from 5 g of the indoline derivative and 3.5 g 1-nitroso-2-naphthol in 60 mL ethanol at 50° C. for 1 h. 2 g of product are isolated after chromatography. Its structure is confirmed by NMR spectroscopy.

Example 4

Synthesis of Compound (4)

This spiroxazine (4) is synthesized from 6 g of the indoline derivative of Example 3 and 4 g 1-nitroso-7-hydroxy-2-naphthol in the ethanol at 60° C. for 1 h. The intermediate product is then methylated with dimethyl sulfate in acetone in the presence of potassium carbonate. 2.2 g of product are isolated after chromatography. Its structure is confirmed by NMR spectroscopy.

Applications

Example 5
Incorporation of Compounds (1) through (4) in a Polyacrylate

General procedure: 10 mg of each one of compounds (1) through (4) are dissolved in tetraethoxylated bisphenol A dimethyl methacrylate, marketed under the name DIACRYL 121 by the company AKZO) and also containing 40 mg of 2',2'-azobis(2-methylbutyronitrile). The solution is then degassed, rendered inert with argon, and then poured in a lens mold made of glass having a diameter of 8 cm and a thickness of 2 mm. The mold is then placed in an oven at 70° C. for 12 h. After removal from the mold, a transparent and rigid lens is obtained. When exposed to solar-type radiation, the glass quickly develops an intense blue coloration and it again becomes colorless in darkness. The photochromic characteristics are given in Table I below. For comparison the characteristics of compounds C1, C2, C3, C4 and C5 of the prior art are also given in Table I below.

TABLE I

| Compound | structure | Wgt % | $\lambda_{max}$ mm | T0 % | TD15 % | IOD | R5 % |
|---|---|---|---|---|---|---|---|
| Ex. 1 | 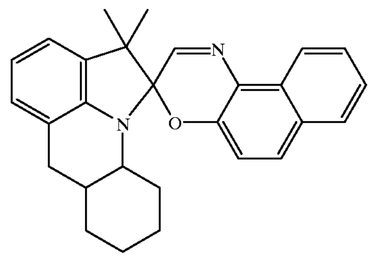 | 0.1 | 614 | 89 | 23 | 0.59 | 72 |
| Ex. 2 | 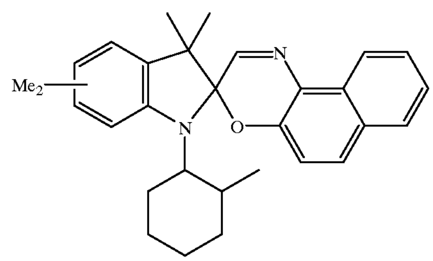 | 0.1 | 624 | 89 | 4.8 | 1.27 | 60 |
| Ex. 3 | 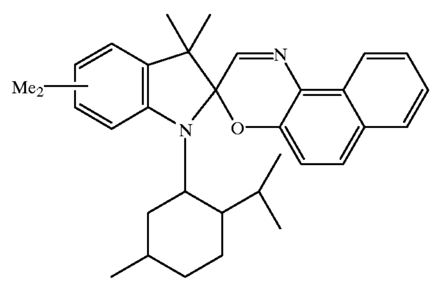 | 0.1 | 624 | 84 | 1.0 | 1.82 | 45 |
| Ex. 4 | 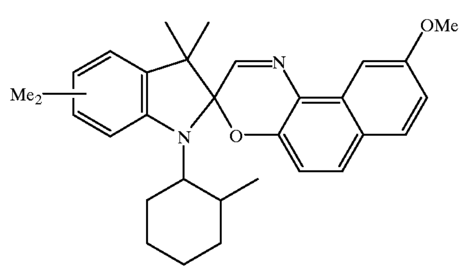 | 0.1 | 620 | 89 | 4.0 | 1.38 | 40 |
| C1 | 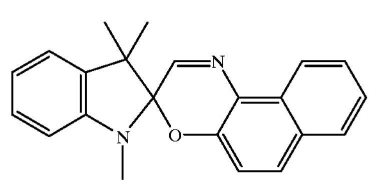 | 0.1 | 604 | 90 | 39 | 0.36 | 83 |

TABLE I-continued

| Compound | structure | Wgt % | λmax nm | T0 % | TD15 % | IOD | R5 % |
|---|---|---|---|---|---|---|---|
| C2 | 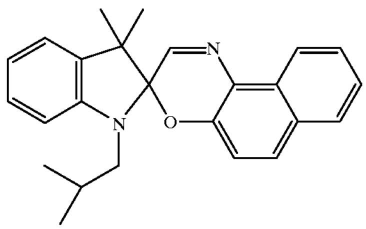 | 0.1 | 610 | 86 | 22 | 0.59 | 74 |
| C3 | 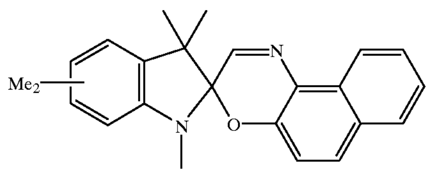 | 0.1 | 616 | 86 | 18 | 0.69 | 68 |
| C4 | 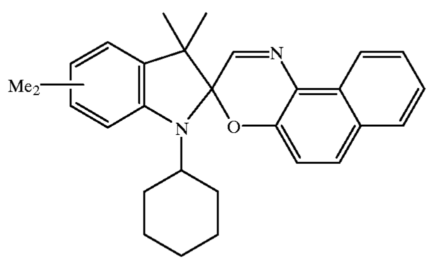 | 0.1 | 624 | 91 | 17 | 0.73 | 70 |
| C5 | 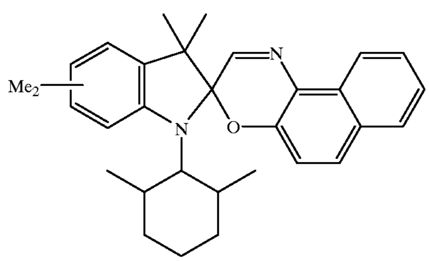 | 0.1 | 620 | 81 | 19 | 0.53 | 63 |

Legends:
λmax measured in D121 in a thickness of 2 mm following exposure to a xenon lamp, 60,000 lx, at 22° C.,
T0 = initial transmission (unactivated state) measured at λmax,
TD15 = transmission after 15 min of exposure measured at λmax,
IOD = Induced optical density (Log(T0/TD15)),
R5 = % of recovery of the initial transmission after 5 min of decoloration.

A comparison of the properties of Example 1 and Comparative Examples C1 and C2, on the one hand, and Examples 2 and 3 and Comparative Examples C3–C5, on the other hand, shows that the compounds of the prior art with analogous structure but without an asymmetric aliphatic monocyclic group according to the invention, do not possess the advantageous combination of the wanted properties. In particular, it is observed that the compounds of the invention have a better compromise between low initial coloration and strong induced optical density.

I claim:

1. A photochromic compound having the following General Formula (I):

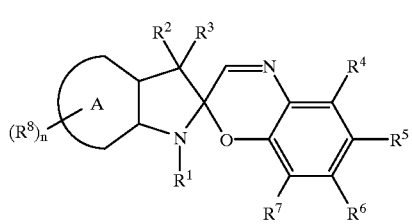

(I)

in which, $R^1$ is an asymmetric aliphatic monocyclic group which is directly connected to the nitrogen atom, having from 5 to 7 members, optionally comprising at least one heteroatom, and having the Formula:

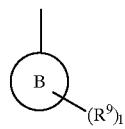

where l=1–12, $R^9$ represents H, a CN group, or an alkyl, alkoxy, dialkylamino, or alkyl ester group optionally substituted with at least one reactive moiety selected from alkenyl, methacryloyl, acryloyl, acryloxyalkyl, methacryloxyalkyl and epoxy moieties, provided that at least one of the $R^9$ is not H, $R^2$ and $R^3$ are identical or different and represent an alkyl group, linear or branched, of 1–12 carbon atoms, an alkenyl group, an alkynyl group, an aryl group, an alkylaryl group, or a cycloalkyl group optionally substituted with at least one reactive moiety selected from alkenyl, methacryloyl, acryloyl, acryloxyalkyl, methacryloxyalkyl, and epoxy moieties, or $R^2$ and $R^3$ combine to form a carbocyclic or heterocyclic group having 5 to 10 atoms optionally substituted with at least one reactive moiety selected from alkenyl, methacryloyl, acryloyl, acryloxyalkyl, methacryloxyalkyl, and epoxy moieties, $R^4$, $R^5$, $R^6$, and $R^7$ are identical or different and represent:
hydrogen,
an alkyl, cycloalkyl, alkenyl, alkynyl, aryl, heteroaryl, aryloxy, or aralkyl group, said group being optionally halogenated; optionally substituted with at least one reactive moiety selected from alkenyl, methacryloyl, acryloyl, acryloxyalkyl, methacryloxyalkyl, and epoxy moieties; or both,
a halogen,
OR, SR, —OCOR, —COOR, wherein R is H; an alkyl, cycloalkyl, or aryl group optionally substituted with at least one reactive moiety selected from alkenyl, methacryloyl, acryloyl, acryloxyalkyl, methacryloxyalkyl, and epoxy moieties; or combinations thereof,
a (poly)ether radical, a (poly)amide radical, a (poly)carbonate radical, a (poly)carbamate radical, a (poly)urea radical, or a (poly)ester radical,
an amino radical which gives rise, once it is bound in (I), to a primary, secondary, or tertiary amine, said amine being alkyl, aryl, or aralkyl, mono- or disubstituted, wherein said amino radical is optionally substituted with at least one reactive moiety selected from alkenyl, methacryloyl, acryloyl, acryloxyalkyl, methacryloxyalkyl, and epoxy moieties, or
an aminocyclic radical containing, optionally, one or more heteroatoms and containing, optionally at least one reactive moiety selected from alkenyl, methacryloyl, acryloyl, acryloxyalkyl, methacryloxyalkyl, and epoxy moieties,
an election withdrawing group, or
a reactive moiety selected from alkenyl, methacryloyl, acryloyl, acryloxyalkyl, methacryloxyalkyl, and epoxy moieties,
where at least two of the radicals, $R^4$, $R^5$, $R^6$, $R^7$, can combine to form at least one aromatic ring having 5 or 6 members or aliphatic ring having 5 to 7 members, said ring(s) comprising, optionally, at least one heteroatom, so as to form at least one heterocyclic ring, the latter being optionally substituted by one or more radicals, which are identical or different and which have the same definition as given above for $R^4$ to $R^7$, A represents a (hetero)aromatic ring which is optionally substituted by one or more radicals $R^8$, which are identical or different and which have the same definition as given above for $R^4$ to $R^7$,
n is a whole number, and, when n≤2, two of the radicals $R^8$ can optionally combine to form at least one aromatic or heteroaromatic ring which is optionally substituted with at least one reactive moiety selected from alkenyl, methacryloyl, acryloyl, acryloxyalkyl, methacryloxyalkyl, and epoxy moieties.

2. A photochromic compound according to claim 1, characterized in that group $R^1$ is selected from the following:

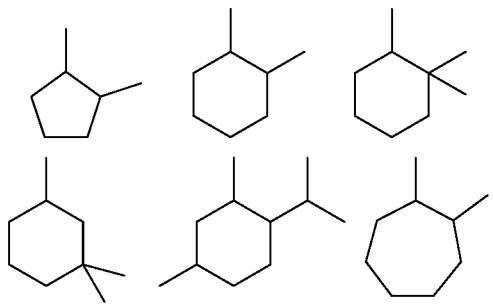

3. A photochromic compound according to claim 1, characterized in that said compound has the General Formula (I'):

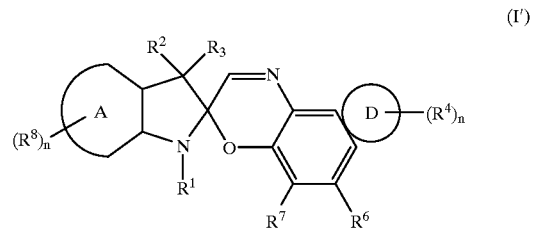

where A and $R^1$–$R^7$ are as defined in the preceding claims, and D is an aromatic or aliphatic ring with 5 to 7 members, optionally comprising a heteroatom, which may or may not be substituted by one or more identical or different radicals having the same definition as given for $R^4$–$R^7$.

4. A photochromic compound according to claim 3, characterized in that said compound has the following General Formula (I"):

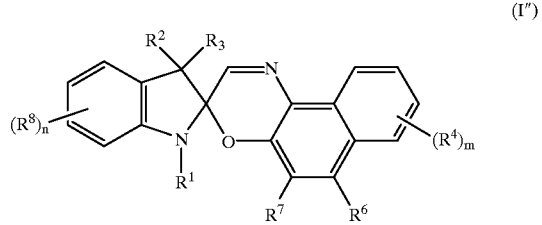

in which $R^1$–$R^4$ and $R^6$–$R^8$ are as defined in claim 1, and n and m take on values from 0 to 4.

5. A photochromic compound according to claim 1, characterized in that the groups $R^1$–$R^9$ of Formula (I) comprise at least one reactive group selected from the following: alkenyl, methacryloyl, acryloyl, acryloxyalkyl, methacryloxyalkyl and epoxy.

6. A photochromic compound according to claim 4, characterized in that said compound has the following Formula:

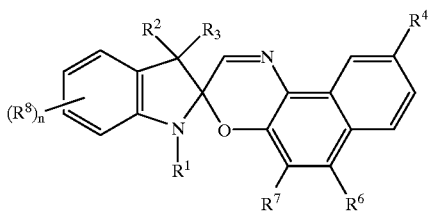

where $R^1 =$

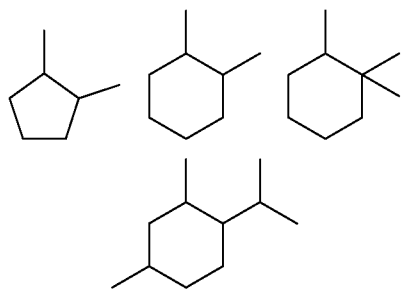

n = 0, 1 or 2,
$R^2, R^3, = C_1–C_5$ alkyl,
$R^4$ = H, OMe,
$R^6$ = H, OMe or amino, and
$R^8$ = H, Me, OMe or $CF_3$.

7. A photochromic compound according to claim 1, wherein, when at least two of the radicals, $R^4, R^5, R^6, R^7$, combine to form at least one aromatic ring having 5 or 6 members, said ring(s) comprise no more than one heteroatom.

8. A photochromic compound according to claim 3, wherein D is an aliphatic ring having 5 to 7 members, optionally comprising a heteroatom, and optionally substituted by one or more identical or different radicals, said radicals having the same definition as given for $R^4$–$R^7$; or wherein D is an aromatic ring having 5 to 7 members, optionally comprising no more than one heteroatom, and optionally substituted by one or more identical or different radicals, said radicals having the same definition as given for $R^4$–$R^7$.

9. A (co)polymer or crosslinkage obtained by polymerization or crosslinking of at least one monomer consisting of at least one photochromic compound according to claim 5.

10. A (co)polymer, characterized in that it is grafted to at least one photochromic compound according to claim 5.

11. A photochromic composition, characterized in that it comprises:
    at least one compound according to claim 1, and
    optionally at least one other photochromic compound, at least one dyes at least one stabilizer, or combinations thereof.

12. A (co)polymer matrix, characterized in that it comprises:
    at least one compound according to claim 1.

13. Matrix according to claim 12, characterized in that the (co)polymer is selected from the following list:
    polyacrylate or polymethacrylate of alkyl, of cycloalkyl, of aryl, or of arylalkyl, (mono, di, tri or tetra) optionally halogenated or comprising at least one ether, ester, carbonate, carbamate, thiocarbamate, urea, or amide group, or combinations thereof;
    polystyrene, polycarbonate, polyepoxy, polyurethane, polythiourethane, polysiloxane, polyacrylonitrile, polyamide, aliphatic or aromatic polyester, polyvinyl acetate, cellulose acetate, cellulose triacetate, cellulose acetate propionate, or polyvinylbutyral; and
    copolymers of two or more types of monomer or mixtures of the above-mentioned polymers.

14. An ophthalmic or sun-protection device comprising:
    at least one compound according to claim 1.

15. An ophthalmic or sun-protection device according to claim 14, characterized in that it consists of a lens.

16. A glass partition or optical device comprising:
    at least one compound according to claim 1.

17. A photochromic composition, characterized in that it comprises:
    at least (co)polymer according to claim 9, and
    optionally at least one other photochromic compound, at least one dye, at least one stabilizer, combinations thereof.

18. A photochromic composition, characterized in that it comprises:
    at least (co)polymer according to claim 10, and
    optionally at least one other photochromic compound, at least one dye, at least one stabilizer, combinations thereof.

19. A (co)polymer matrix, characterized in that it comprises:
    at least one (co)polymer according to claim 9.

20. Matrix according to claim 19, characterized in that the (co)polymer is selected from the following list:
    polyacrylate or polymethacrylate of alkyl, of cycloalkyl, of aryl, or of arylalkyl, (mono, di, tri or tetra) optionally halogenated or comprising at least one ether, ester, carbonate, carbamate, thiocarbamate, urea, or amide group, or combinations thereof;
    polystyrene, polycarbonate, polyepoxy, polyurethane, polythiourethane, polysiloxane, polyacrylonitrile, polyamide, aliphatic or aromatic polyester, polyvinyl acetate, cellulose acetate, cellulose triacetate, cellulose acetate propionate, or polyvinylbutyral; and
    copolymers of two or more types of monomer or mixtures of the above-mentioned polymers.

21. A (co)polymer matrix, characterized in that it comprises:
    at least one (co)polymer according to claim 10.

22. Matrix according to claim 19, characterized in that the (co)polymer is selected from the following list:
    polyacrylate or polymethacrylate of alkyl, of cycloalkyl, of aryl, or of arylalkyl, (mono, di, tri or tetra) optionally halogenated or comprising at least one ether, ester, carbonate, carbamate, thiocarbamate, urea, or amide group, or combinations thereof;

polystyrene, polycarbonate, polyepoxy, polyurethane, polythiourethane, polysiloxane, polyacrylonitrile, polyamide, aliphatic or aromatic polyester, polyvinyl acetate, cellulose acetate, cellulose triacetate, cellulose acetate propionate, or polyvinylbutyral; and copolymers of two or more types of monomer or mixtures of the above-mentioned polymers.

23. An ophthalmic or sun-protection device comprising:

at least one (co)polymer according to claim 9.

24. An ophthalmic or sun-protection device according to claim 23, characterized in that it consists of a lens.

25. An ophthalmic or sun-protection device comprising:

at least one (co)polymer according to claim 10.

26. An ophthalmic or sun-protection device according to claim 25, characterized in that it consists of a lens.

27. A glass partition or optical device comprising:

at least one (co)polymer according to claim 9.

28. A glass partition or optical device comprising:

at least one (co)polymer according to claim 10.

* * * * *

UNITED STATES PATENT AND TRADEMARK OFFICE
CERTIFICATE OF CORRECTION

PATENT NO. : 6,004,486
DATED : December 21, 1999
INVENTOR(S) : You-Ping Chan

It is certified that error appears in the above-identified patent and that said Letters Patent is hereby corrected as shown below:

| Col. | Line | Description |
|------|------|-------------|
| 16 | 5 | Change "$n \leq 2$" to --$n \geq 2$-- |
| 17 | 66 | Change "dyes" to --dye,-- |

Signed and Sealed this

Thirty-first Day of October, 2000

Attest:

Q. TODD DICKINSON

Attesting Officer

Director of Patents and Trademarks